United States Patent [19]
Tajima

[11] Patent Number: 5,919,706
[45] Date of Patent: Jul. 6, 1999

[54] METHOD FOR SUCKING/DETERMINING LIQUID AND PIPETTING DEVICE DRIVEN AND CONTROLLED ACCORDING TO METHOD

[75] Inventor: Hideji Tajima, Tokyo, Japan

[73] Assignee: Precision System Science Co., Ltd., Tokyo, Japan

[21] Appl. No.: 08/750,428
[22] PCT Filed: Apr. 11, 1996
[86] PCT No.: PCT/JP96/00993
  § 371 Date: Dec. 11, 1996
  § 102(e) Date: Dec. 11, 1996
[87] PCT Pub. No.: WO96/32649
  PCT Pub. Date: Oct. 17, 1996

[30] Foreign Application Priority Data

Apr. 11, 1995 [JP] Japan .................................... 7-109157
Apr. 9, 1996 [JP] Japan .................................... 8-111091

[51] Int. Cl.[6] ............................ G01N 35/06; G01F 23/28
[52] U.S. Cl. ........................... 436/54; 436/49; 436/180; 422/67; 422/81; 422/100; 422/106; 73/863.02; 73/864.01; 73/864.21
[58] Field of Search ............................... 422/63, 67, 100, 422/81, 105, 106, 108; 436/43, 49, 54, 50, 165, 180; 73/863.01, 863.02, 293, 864.01, 864.21, 864.81, 864.85

[56] References Cited

U.S. PATENT DOCUMENTS 4,844,870  7/1989  Rasmussen et al. ..................... 422/68
4,939,925  7/1990  Sakuma et al. .......................... 73/61.4
4,944,922  7/1990  Hayashi .................................. 422/100
5,271,902  12/1993 Sakka et al. ............................ 422/100

FOREIGN PATENT DOCUMENTS

61-254833  11/1986  Japan .
04-204136  7/1991  Japan .
03-246423  11/1991  Japan .
04-84729  3/1992  Japan .
06-191501  7/1994  Japan .

*Primary Examiner*—Long V. Le
*Attorney, Agent, or Firm*—McDermott, Will & Emery

[57] ABSTRACT

In the present invention, a disposable tip or a tip of a cleaning system is attached to a lower edge section of a nozzle, and the nozzle detects a liquid level by receiving fluctuation of a light close to the disposable tip or to an opening section at a lower end of the tip in the cleaning system, for instance, a light reflected from the liquid surface. In the present invention, not only the liquid level is detected, but also a liquid is filled in the disposable tip or the tip of a cleaning system detachably attached to the nozzle, a light is passed through the liquid in the disposable tip or the tip of a cleaning system, and a change of a light amount of the sucked liquid is detected, so that, for instance, a suction rate of the liquid, transparency thereof, contaminated by bubbles therein, clogging and a state wherein water has been exhausted are determined.

24 Claims, 9 Drawing Sheets

METHOD FOR SUCKING/DETERMINING LIQUID AND PIPETTING DEVICE DRIVEN AND CONTROLLED ACCORDING TO METHOD

TECHNICAL FIELD

The present invention relates to an entirely new method for sucking/determining a liquid and a pipetting device driven and controlled according to the method, and more particularly to a method for sucking/determining a liquid in which driving required for upward/downward movement of a nozzle for sucking a liquid such as a sample for a blood serum and a reagent as well as for pipetting a liquid to cylinders each for sucking and discharging the liquid is accurately controlled, so that a liquid level and a sucking rate of a liquid by the nozzle, and contamination of foreign matters therein such as bubbles or fibrins or the like in the liquid can accurately be detected, as well as to a pipetting device driven and controlled according to the method.

BACKGROUND ART

Generally, important matters required for enhancing pipetting precision are to detect a level of a blood serum sample and a reagent or similar liquid, to measure a pipetting rate thereof, to measure an absolute sucking rate thereof, to adhere the liquid to the outside of the nozzle, and to detect contamination thereof by foreign matters such as bubbles and fibrins.

For this reason, conventionally, a method has been employed, in which an electrode is immersed in the liquid together with the nozzle and the liquid level is detected according to a conductive state with the electrode so that an inserting rate (distance) of the nozzle to the liquid is controlled, but in the case of this method, the electrode must be immersed into the liquid, so that the electrode must be washed after each measurement thereof to prevent cross contamination, and as a result, there have been such problems as that a device becomes complicated, and that size and cost of the device increase.

Then, recently a method of detecting a liquid level using a pressure sensor was proposed. In this method, a sucking pressure of the nozzle when a vapor is sucked is different from that when a liquid is sucked, so that the liquid level is detected by detecting the difference between the pressures, whereby an inserting rate (distance) of the nozzle to the liquid is controlled, and for this reason only the nozzle is contacted with the liquid, and the method has such advantages as that a cleaning function is not required, which makes it possible to simplify the device as well as to reduce the costs.

However, the method of detecting a liquid level using a pressure sensor has several problems such as that the resolution is low and the sensitivity is not high, and also that the method is easily affected by an atmospheric pressure as well as by pressure change due to the sucked air, and also affected by vibrations generated due to upward/downward movement of the nozzle as well as by a noise of the pipetting device itself or a change of a voltage, and for this reason malfunction thereof occurs quite often, and the reliability thereof as a measuring means is quite low.

An optical liquid level detecting means is far more effective as a means to solve the problems as described above, and various means in which both an optical fiber for irradiating a light therethrough and an optical fiber for receiving a light are provided outside the nozzle for receiving a reflected light from a liquid level with the optical fiber for receiving a light to detect the level thereby are proposed for the liquid level detecting methods based on the conventional technology.

However, in the liquid level detecting means using a light for detecting a liquid level based on the conventional technology, in which both a fiber for irradiating a light therethrough and an optical fiber for receiving a light are provided outside the nozzle for catching a reflected light from a liquid level with the optical fiber for receiving a light to detect the level thereby, these fibers have to be inserted in parallel to each other together with the nozzle into a vessel for a liquid, and for this reason it can not be denied that the method has a possibility of cross contamination caused by the fiber contacting with the liquid adhered to the wall surface of the vessel for a liquid, and also the amount of light caught by the optical fiber for receiving a light is extremely small, which makes it difficult to accurately detect a liquid level, and in addition the extremely minute control is required, which is difficult because there also occur some cases where a timing for receiving the reflected light is shifted or a light can not be received by the fact that the liquid level becomes slightly wavy due to vibrations of the device.

The present invention was made to solve the problems as described above, and it is an object of the present invention to provide an entirely new method of sucking/determining a liquid, including, for instance, detection of a liquid level in which a light receiving body is provided in a nozzle, and fluctuation of a light in a disposable tip such as a pipetting tip or in an opening section at the lower end of a tip of a cleaning system are detected thereby from the side of nozzle under circumstances similar to seeing the other opening section from one end of a tunnel, so that it is possible to extremely sensitively detect a liquid level, contamination by foreign matters therein, or an interface between liquids each having a different color without being affected by the wavy liquid level, as well as to provide a pipetting device driven and controlled according to the method. Namely, a basic principle of the present invention is characterized in that the various types of detecting operation are carried out by catching a moment as if a light instantly changed shows fluctuation in a flash when a near-by substance in a space cut off from the outside of the environment is changed, for instance, from vapor to liquid.

DISCLOSURE OF INVENTION

To achieve the object as described above, in the method of sucking/determining a liquid according to the present invention, it is essential to detect variations of lights caused by a liquid accommodated in the vessel with the nozzle for sucking the liquid.

In the present invention, a disposable tip or a tip of a cleaning system is attached to a lower edge section of a nozzle, and the nozzle detects a liquid level by receiving fluctuation of a light close to the disposable tip or to an opening section at a lower end of the tip in the cleaning system, for instance, a light reflected from the liquid surface.

Furthermore, in the present invention, not only the liquid level is detected, but also a liquid is filled in the disposable tip or the tip of a cleaning system detachably attached to the nozzle, a light is passed through the liquid in the disposable chip or the tip of a cleaning system, and a change of a light amount of the sucked liquid is detected, so that, for instance, a suction rate of the liquid, transparency thereof, contamination by bubbles therein, clogging and a state wherein water has been exhausted are determined.

And furthermore, in the present invention, fluctuation of a light wave length can be detected and a change of color is checked by the nozzle, whereby a liquid level can also be detected. The color change can be detected according to the nozzle to detect a color of the colored vessel accommodating a liquid therein through the liquid, or according to the nozzle to detect a color of a rack or a color of a holder in which a transparent vessel accommodating a liquid therein is vertically provided, through the liquid. It is needless to say that detection of color change herein includes detecting an interface on which layers are separated by identifying a color of a blood clot or a blood coagulant in a process, for instance, in which the nozzle is moving downward while sucking a blood serum.

In the present invention, the light is not limited to a case of a light which is directly received from the disposable chip or from the opening section at the lower end of the tip of a cleaning system attached to the nozzle, and, for instance, a light may be irradiated or received through a transparent disposable tip or a tip of a cleaning system.

In the present invention, it is desirable that the nozzle itself is formed with a light transmitting material in a tubular form, or only the lower edge section thereof is formed with the light transparent material, or a flux of optical fibers are provided therein.

In this case, it is desirable that a lens body is provided in the tip section of a disposable tip or a tip of a cleaning system in the nozzle, for instance, in a slightly lower side than the opening section in the lower end of the disposable tip or the lower edge thereof, so that the lens can be focused at a position where fluctuation of an amount of received light can be checked with high-precision. The lens may be used depending on the form or length of the tip, diameter of the opening section, light-proof property or the like, and in this case, the lens may be provided in any of a light irradiating section and/or a light receiving section, and a concave lens may be used as well as a convex lens, or a plurality of concave and convex lenses may be combined to be used.

In the present invention, a light is supplied to a liquid accommodated in a vessel through nozzle itself or through a fiber for light irradiation and a light receiving fiber each provided inside the nozzle, or is supplied from the outside of the nozzle.

A supply of a light from the outside of the nozzle includes irradiation of a light from the outside of a transparent vessel for containing a liquid to said liquid, or irradiation of a light to a liquid through a disposable tip or a tip of in a cleaning system in addition to irradiation of a light from an optical fiber provided near the outside of the nozzle to the liquid. It is needless to say that, irradiation of a light is not limited to a case where a light is irradiated continuously, but a light may be irradiated by blinking it at certain time intervals.

Data obtained by the method for sucking/determining a liquid having the construction as described above is preferably used as data for controlling a pipetting device in which driving required for pipetting a liquid to cylinders for moving upward/downward the nozzle as well as for sucking/discharging a liquid is controlled.

BEST MODE FOR CARRYING OUT INVENTION

Detailed description is made for embodiments of the present invention with reference to the related drawings.

Figure 1:
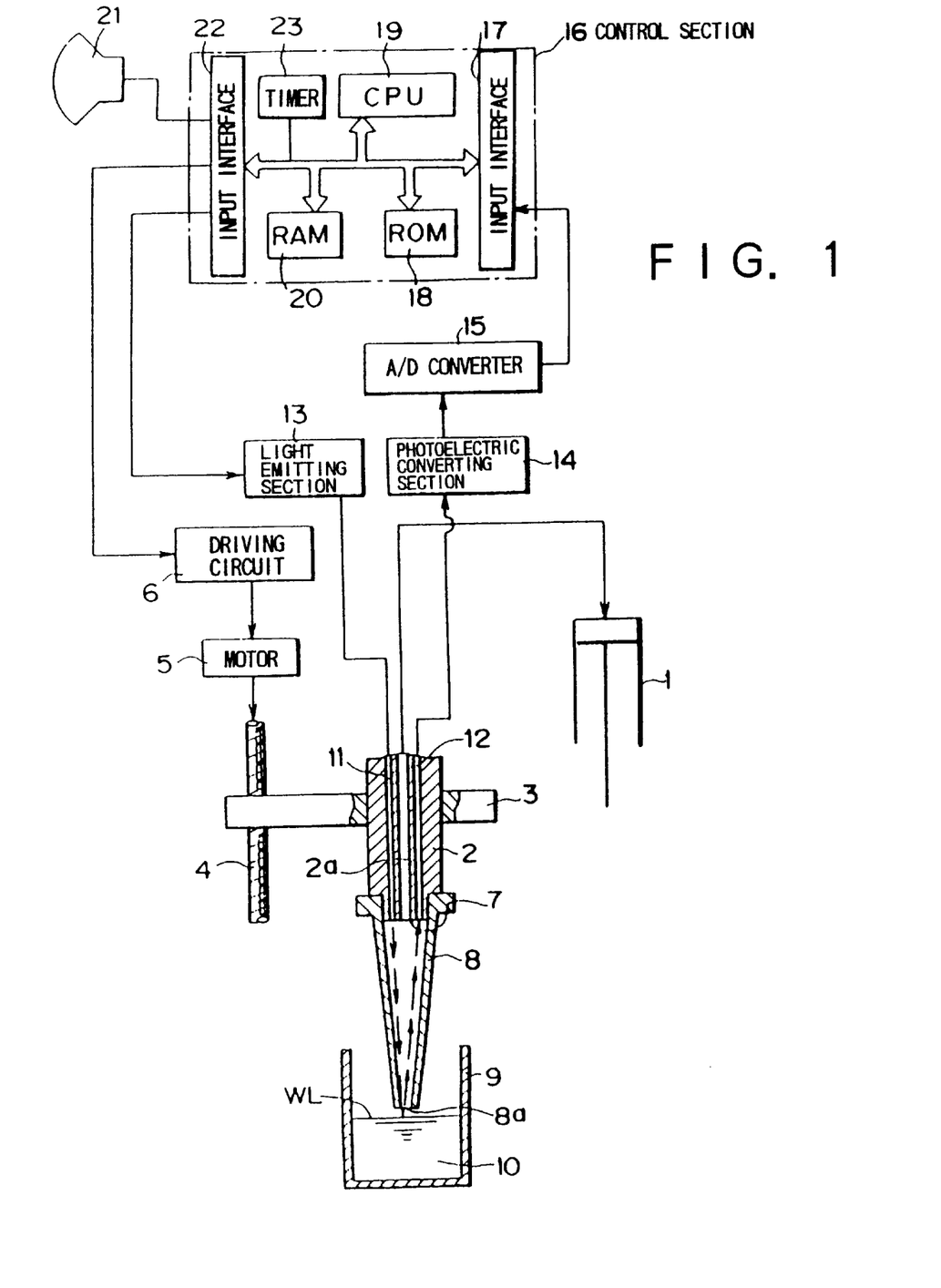
FIG. 1 is an explanatory view showing schematic configuration of a pipetting device according to a first embodiment of the present invention.

FIG. 1 shows a schematic configuration of a pipetting device to which the method for sucking/determining a liquid according to the first embodiment of the present invention is applied, and the pipetting device basically comprises a nozzle 2 communicated with and connected to a cylinder 1; an arm 3 for holding the nozzle 2; a drive mechanism 4 for moving the arm 3 upward and downward; a motor 5 for operating the drive mechanism 4; a driving circuit 6 for controlling regular/reverse rotation of the motor 5; and a disposable tip 8 detachably attached to the lower edge section 7 of the nozzle 2.

The nozzle 2 is moved downward at a specified position by the drive mechanism, the liquid level WL is detected by a liquid level detecting mechanism described later, then a liquid 10 such as a serum or a reagent accommodated in a vessel 9 is sucked, and then the pipetting device moves upward to discharge the sucked liquid to another vessel (not shown herein). It should be noted that each of the basic configurations of the pipetting devices according to the present invention is the same as that which is well known so long as a particular mention is not made in the present specification, so that detailed description thereof is omitted herein.

In the nozzle 2, a bore hole 2a through which a liquid is passed along the longitudinal direction in the center section of the nozzle 2 constructed the same as for a nozzle based on the conventional technology is formed, the upper edge section of the bore hole 2a is communicated with and connected to the cylinder 1, and at the same time in the nozzle 2, the liquid level detecting mechanism comprising a light irradiating body 11 having an optical fiber or a flux of more than two optical fibers and a light receiving body 12 is incorporated, and the lower edge sections of the light irradiating body 11 and of the light receiving body 12 are arranged each in its exposed state in the bottom surface of the lower edge section 7 in the nozzle 2 formed in a reversed convex shape.

Connected to the upper edge section of the light irradiating body 11 is a light emitting section 13 for emitting and supplying a light. The light emitting section 13 supplies a light to the light irradiating body 11, the light irradiated from the lower edge section of the light irradiating body 11 is reflected on the liquid surface WL and is received by the light receiving body 12, then the received and reflected light is converted to a voltage by a photoelectric converting section 14 connected to the upper edge section of the light receiving body 12, a signal for the converted voltage value is sent to an A/D converter 15 for converting it to a digital signal, the digital signal from the A/D converter 15 is received by the control section 16 (e.g. microcomputer) for executing various types of controlling, and the data for a control signal outputted from the control section 16 is displayed on a display means 21 comprising a CRT or the like.

The control section 16 comprises an input interface 17 for receiving a digital data signal from the A/D converter 15; a ROM 18 for storing therein a program required for computing an inputted signal; a CPU 19 for executing a specified computing according to a program stored in the ROM 18; a RAM 20 for temporarily storing therein a result of computing or data; an output interface 22 for outputting a control signal to various objects to be controlled or to the display means 21 in the device; and a timer 23. It should be noted that the CPU 19 previously stores therein, for instance, specified values or predetermined values identifying a reflected state of a light, executes computing and determining such as comparing the specified values or the predetermined values to measured values, and transmits an instruction for driving and controlling each of the mechanisms according to the determination.

Intrusion of light from outside or leakage of light transmitted through light irradiating body 11 and light receiving body 12 can be prevented without fail by cutting off light with light-proof film layers in which the peripheral surface of the nozzle 2 and an internal peripheral surface of the bore hole 2a, or a peripheral surface of the light irradiating body 11 and the light receiving body 12 are subjected to black coloring or the like or to mirroring respectively, so that a clear light signal without any noise can be transmitted, which makes it possible to control more smoothly the control section. It is needless to say that each of the lower edge sections of the light irradiating body 11 and light receiving body 12 is formed, for instance, to a convex lens form, and also formed to a form in which the transmitted light is focused to near the opening at the lower end section of the disposable tip 8, and the light reflected on the liquid surface enters into the nozzle 2 for being detected.

Next, a description is made for operations of detecting a liquid level in the pipetting device constructed as described above.

When liquid level detection is instructed to the control section 16, the control section 16 outputs a control signal to the light emitting section 13, and the light emitting section 13 supplies a light to the light irradiating body 11. A supply of the light is executed continuously or executed by blinking it at certain time intervals. Then, simultaneously when the light is supplied, the control section 16 also outputs a control signal to the driving circuit 6, and the driving circuit 6 moves the arm 3 downward into the vessel 9 containing a liquid by means of the motor 5. Further, the control section 16 starts moving the arms downward and the timer 23 incorporated therein starts counting.

In association with the downward movement of the arm 3, the light irradiated from the light irradiating body 11 into a disposable tip 8 is, as shown in FIG. 1, irradiated from the opening section 8a at the lower end thereof onto a liquid surface WL, and the light reflected on the liquid surface WL reenters again from the opening section 8a at the lower end into the disposable tip 8 and is received by the light receiving body 12.

Namely, the light outputted from the opening section 8a at the lower end of the disposable tip 8 through the light irradiating body 11 and irradiated to the liquid surface WL, when the opening section 8a at the lower end thereof is above the liquid surface, is reflected on the liquid surface WL, or passes under the liquid surface, so that the light hardly returns to the opening 8a at the lower end thereof, and for this reason, the amount of a light received by the light receiving body 12 is at a low level.

The amount of light received by the light receiving body 12 while the disposable tip 8 is moving downward to a certain position does not change much.

Then, when a disposable chip 8 has moved downward to the certain position, and light going exiting from the opening section 8a at the lower end thereof through the light irradiating body 11 and irradiated to the liquid surface WL is reflected on the liquid surface WL and again received into the disposable tip 8 from the opening section 8a at the lower end thereof, the amount of light in the disposable tip 8 cut off from the outside environment momentarily reaches a high level, so that the light amount at that moment is detected, and the detected amount thereof is compared to a specified value or identified as a predetermined value. In this case, a reflected light can be caught at more accurate timing if the cylinder 1 is moved downward while sucking a liquid.

The photoelectric converting section 14 successively converts the change of the light amount during the time described above to a voltage value, and the control section 16 compares the voltage value to the specified value or identifies that as a predetermined value, and immediately terminates the downward movement of the arm 3 and/or the sucking operation by the cylinder 1.

The signal for voltage value obtained as described above is converted to a digital signal with the A/D converter 15, and a fluctuations of the series of voltages can be stored in the control section 16.

The control section 16 measures with the timer 23 a period of time required from start of measurement until a point of time when the maximum voltage value is obtained, and computes a liquid level WL corresponding to a time previously stored therein with the CPU 19. The data as to whether the liquid level WL has been detected or not is displayed on the display means 21 comprising a CRT or the like. In the embodiment, however, description was made for a case where a liquid level was detected by using the timer 23 as an example, but the present invention is not limited to the case described above, and it is possible to detect a liquid level (position for driving) by using, for instance, a well known pulse counter or an encoder.

When the liquid level is detected as described above, the control section 16 provides an instruction to the driving circuit 6 to move the arm 3 downward, and the arm 3 descends for the distance instructed by the control section 16 according to the instruction, so that the tip section of the disposable chip 8 is inserted into the liquid 10, and a required amount of the liquid 10 in the vessel 9 for a liquid is sucked into the disposable chip 8 with the cylinder 1 sucking the liquid according to an instruction by the control section 16.

In the pipetting device according to the embodiment, as described above, a momentary specified value or a momentary predetermined value when fluctuation of the amount of received light reflected on the liquid surface in a space section formed by the disposable tip 8 is extremely different can be caught as a noiseless clear signal without being affected by the outside, so that a liquid level can be detected with high-precision, and the nozzle 2 itself is not contacted with the inside surface of the vessel 9 containing a liquid, which makes it possible to prevent cross contamination without fail.

Figure 2:
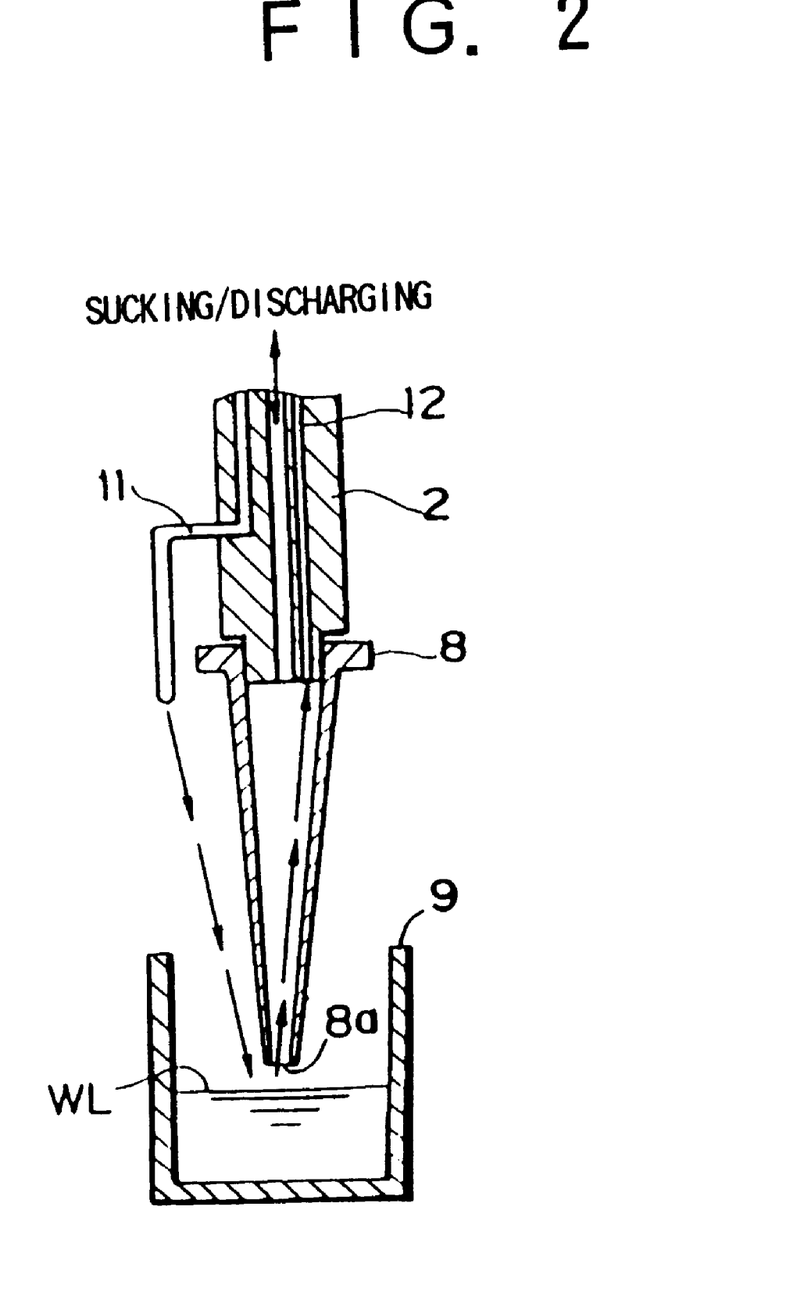
FIG. 2 is an explanatory view showing schematic configuration of a pipetting device according to a second embodiment of the present invention.

It should be noted that, in the first embodiment, description was made for a case where the lower edge section of the light irradiating body 11 is exposed at the lower edge section of the nozzle 2 as an example, but, as described in the second embodiment shown in FIG. 2, the same effect can be obtained even if the lower edge section of the light irradiating body 11 is led to the outside of the nozzle 2, and a light is irradiated from the outside of nozzle 2, is reflected on the liquid surface WL, and the light reflected thereon is received by the light receiving body 12 provided in the lower edge section of the nozzle 2 through the opening section 8$a$ at the lower end thereof.

Figure 3:
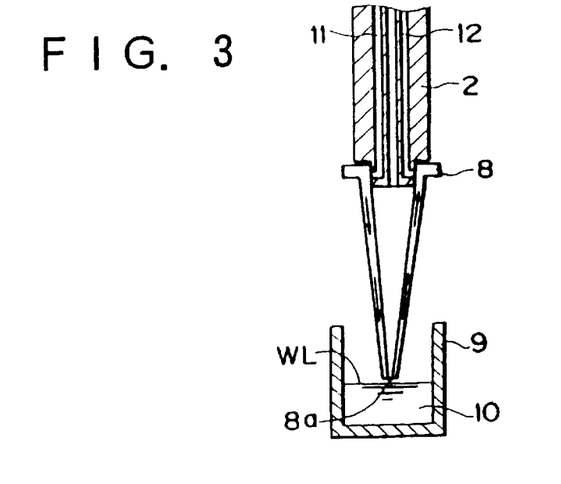
FIG. 3 is an explanatory view showing schematic configuration of a pipetting device according to a third embodiment of the present invention.

FIG. 3 shows the third embodiment according to the present invention, and in this embodiment, the device can also be constructed so that the lower edge sections of the light irradiating body 11 and the light receiving body 12 are provided in the side section of the lower edge section 7 of the nozzle 2 in the exposed state respectively, and the disposable tip 8 may be formed with a transparent and photoconductive material, and in that case a light irradiated from the light irradiating body 11 passes through the disposable tip 8 and is irradiated to the liquid surface WL through the opening section 8$a$ at the lower end of the disposable tip 8, the reflected light again passes through the disposable tip 8, and the amount of the light can be detected with the light receiving body 12.

Figure 4:
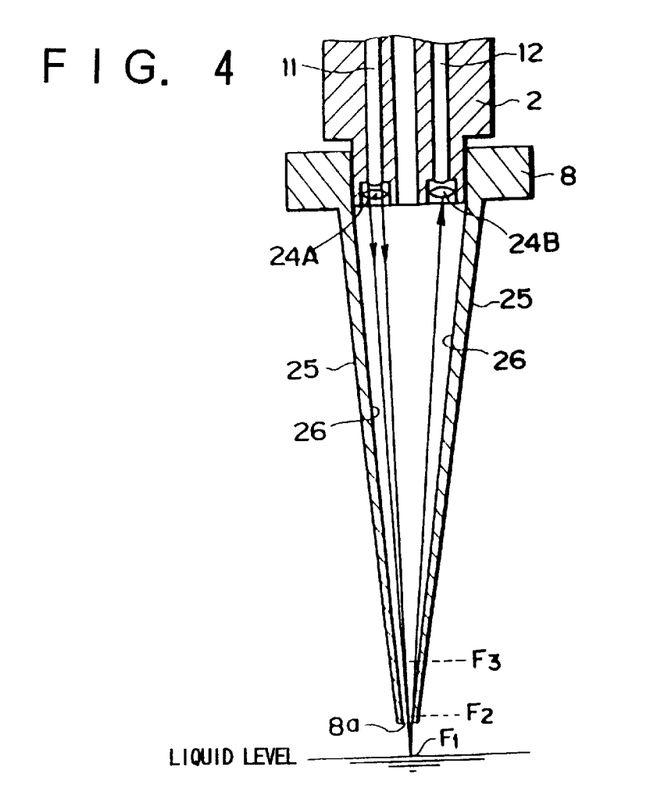
FIG. 4 is a cross-sectional view showing a state in which a lens body is provided in the light irradiating body and a light receiving body in the pipetting device according to a fourth embodiment of the present invention.

FIG. 4 shows the fourth embodiment according to the present invention, and in this embodiment, focusing lenses 24A, 24B are provided each at a positions lower than each of the lower edge sections of the light irradiating body 11 and the light receiving body 12, the light irradiated from the light irradiating body 11 is focused at a point $F_1$ on the liquid surface WL, so that a brighter reflected light can be received, and the resolution can further be improved.

The focusing lenses 24A, 24B may be concave lenses or convex lenses, or may be a combination thereof, and also the irradiated light may be focused not only on the point $F_1$ on the liquid surface, but also at a center portion $F_2$ of the opening section 8$a$ at the lower end of the disposable tip 8, or at a position $F_3$ slightly above the opening section 8$a$ at the lower end of the disposable tip 8 or at any other appropriate position so long as a change in a quantity of received light can be accurately detected. The focusing lenses 24A, 24B may be provided in either one of the light irradiating body 11 or the light receiving body 12, but in the present embodiment, a lens is always provided in the side of the light receiving body 12. However, in the present invention, the focusing lens described above may not always be provided therein, and it is quite possible to detect how high the liquid level WL is even if a light irradiated from the light irradiating body 11 is supplied to the liquid surface without focusing the light thereon.

On the external and internal peripheral surfaces of the tip 8 shown in FIG. 4, light-proof film layers 25, 26 each subjected to black coloring or mirroring are formed respectively. By forming the light-proof film layers 25, 26 each on the external peripheral surface as well as on the internal peripheral surface of the disposable tip 8, intrusion of a light from the outside into the tip and leakage of light transmitted therethrough can be prevented without fail, so that a clear light signal without any noise can be received with the light receiving body 12, and control can be more smoothly provided.

Figure 5:
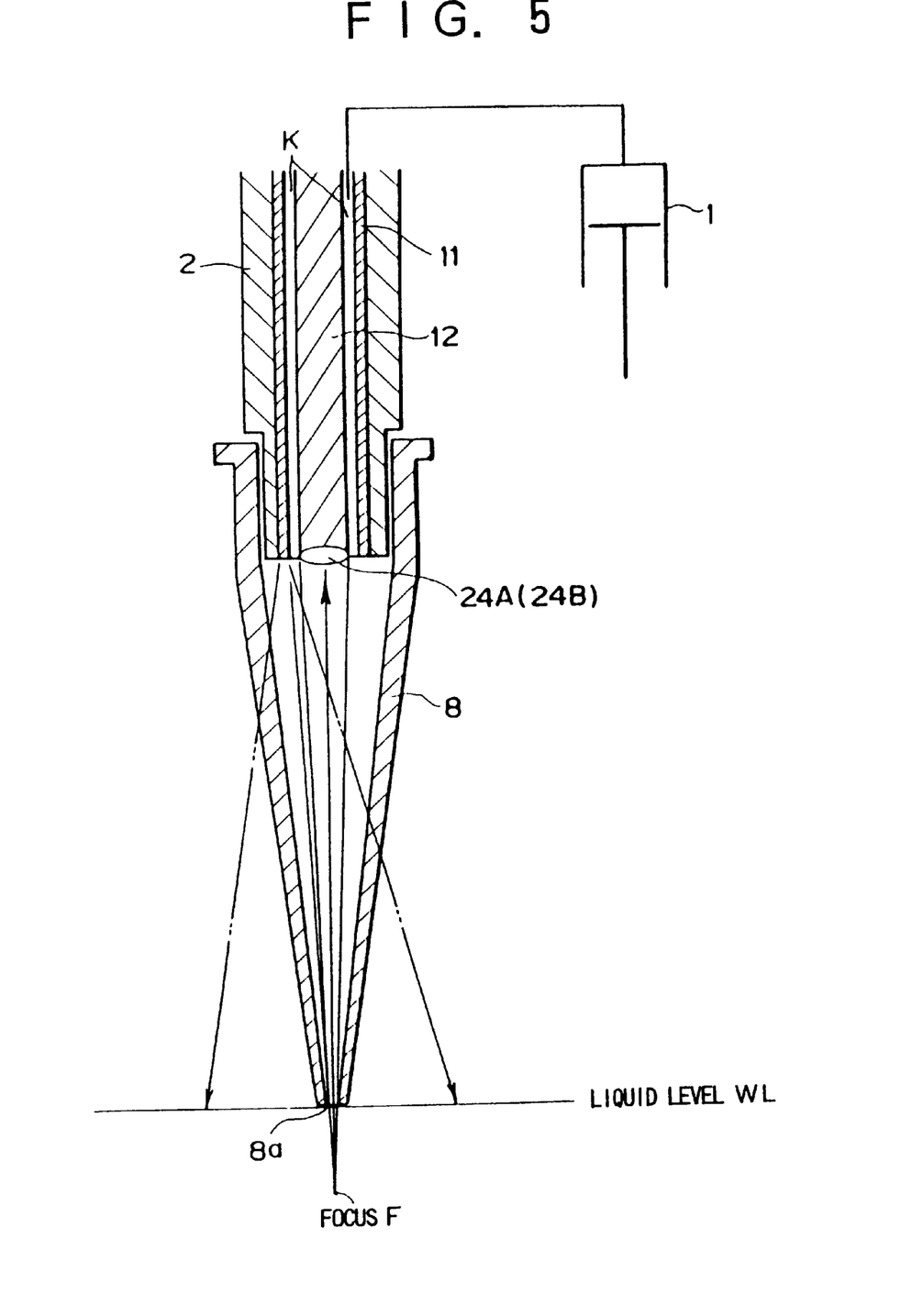
FIG. 5 is an explanatory view showing schematic configuration of a pipetting device according to a fifth embodiment of the present invention.

FIG. 5 shows a configuration of a nozzle section in a pipetting device according to a fifth embodiment of the present invention, and the embodiment shows a case where the light receiving body 12 is provided at the center of the nozzle 2, and outside the light receiving body 12 a ring-shaped light irradiating body 11 is provided at a specified gap therefrom, and the annularly-shaped gap formed between the light irradiating body 11 and light receiving body 12 is communicated with and connected to the cylinder 1 as a suction conduit K. The other configuration features and effects thereof besides those described above are the same as those in the first embodiment, so that the same reference numerals used in the first embodiment are assigned to the portions corresponding thereto in the figure and detailed description thereof is omitted herein.

Figure 6:
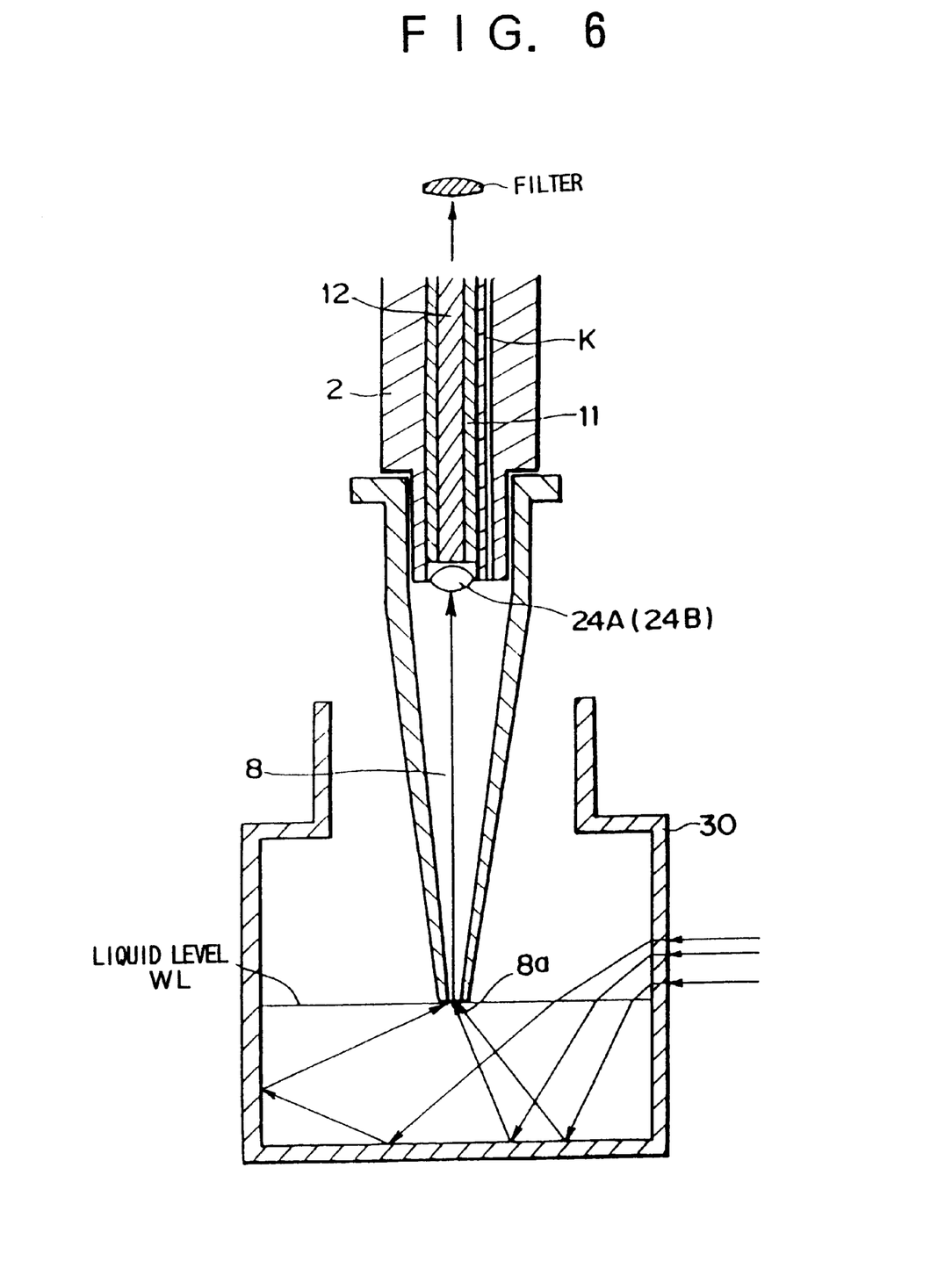
FIG. 6 is an explanatory view showing a schematic configuration of a pipetting device according to a sixth embodiment of the present invention.

FIG. 6 shows a pipetting device according to a sixth embodiment of the present invention, and the embodiment shows a case where the invention is applied to a device for pipetting, for instance, a reagent or other liquid accommodated in a bottle 30, in which the light receiving body 12 is provided at the center of the nozzle 2, the light irradiating body 11 formed in a ring shape is provided outside the light receiving body 12, and a suction conduit K for sucking the liquid in the bottle 30 is provided outside the light irradiating body 11. The and other configuration features and effects thereof besides those described above are the same as those in the first embodiment, that the same reference numerals used in the first embodiment are assigned to the portions corresponding thereto in the figure and detailed description thereof is omitted herein.

Figure 7:
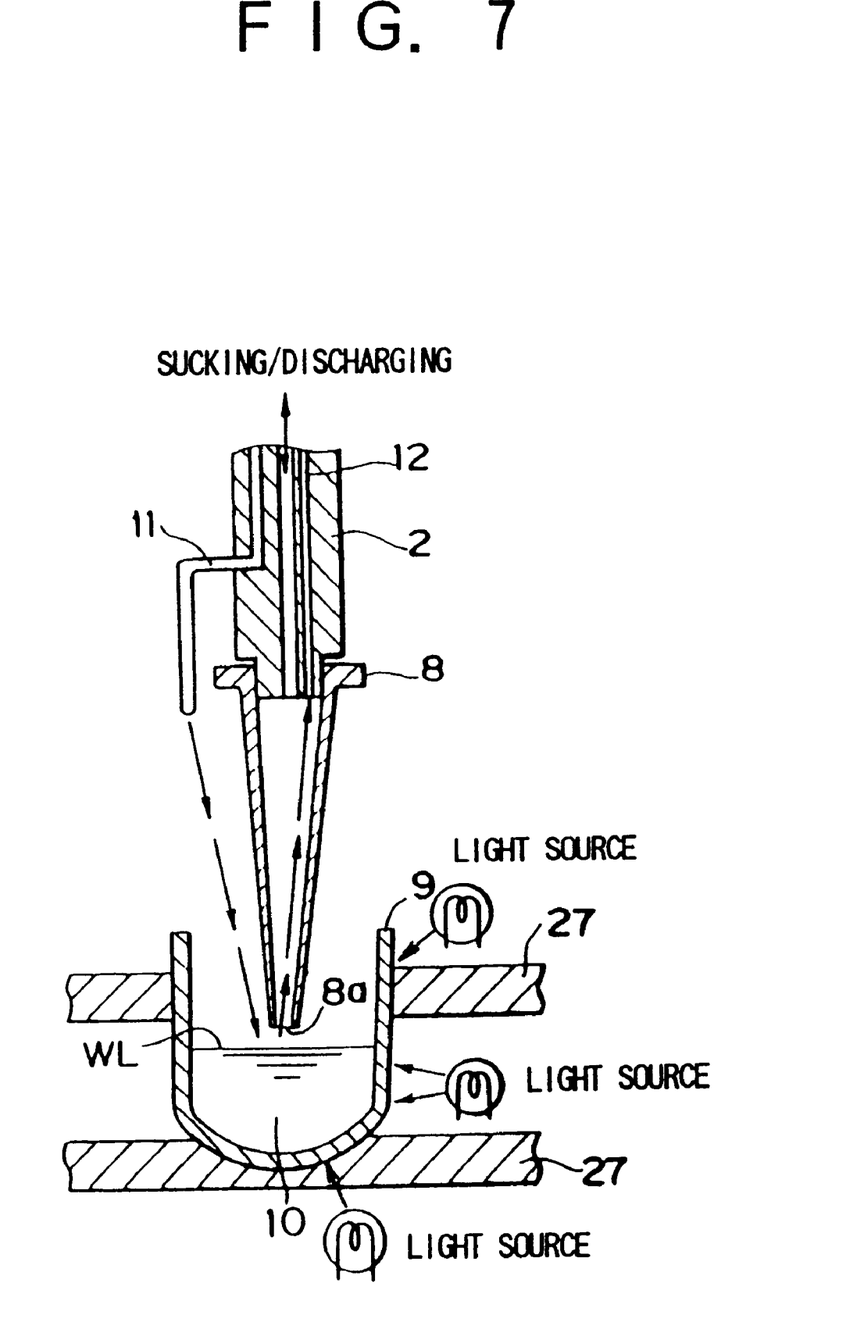
FIG. 7 is an explanatory view showing schematic configuration of a pipetting device according to a seventh embodiment of the present invention.

FIG. 7 shows a seventh embodiment of the present invention, and in this embodiment, the same configuration in the nozzle side is formed as that in the second embodiment shown in FIG. 2, and a light is irradiated from the outside of a colored or transparent vessel 9 containing a liquid or from the outside of a rack 27 in which the vessel 9 is vertically provided, an amount of a light or change of color (a light wave length) reflected on the surface of the liquid 10 is detected through the liquid 10 contained in the vessel 9. It should be noted that detection according to color as described above can also be executed in the configuration of the first embodiment.

As described above, as in a case where a light amount is detected, the position of a liquid level WL can be detected even if a change of a light wavelength (color) is detected by the light receiving body 12.

By constructing the device so that color can be detected as described above, in a case where two colors of liquid in the vessel 9, for instance, a blood serum and a blood clot or a blood serum, a blood coagulant, and a blood clot are separated into layers by centrifugation and accommodated therein, an interface between a blood serum and other substances can be detected according to a change of the color thereof by slowly moving down the disposable tip 8, which makes it possible to prevent contamination of the chip and a blood coagulant or a blood clot effectively and without fail.

Figure 8:
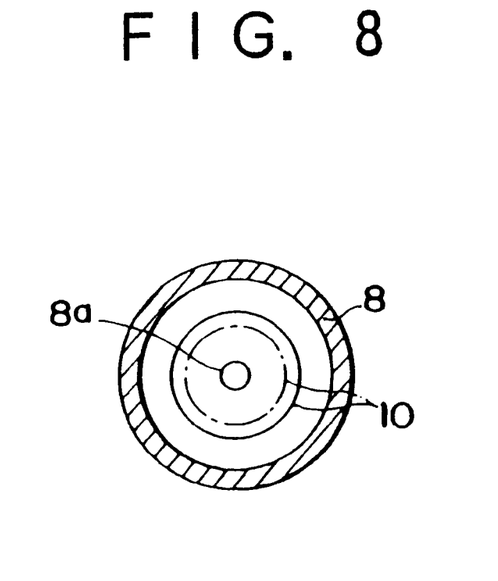
FIG. 8 is an explanatory transverse sectional view showing a level (a surface area) of a liquid to be sucked in a case where it is detected whether a sucked amount of liquid is sufficient or not with the pipetting device according to an eighth embodiment of the present invention.

FIG. 8 shows an eighth embodiment of the present invention, and in this embodiment, determination can easily be made as to whether a sucked amount of a liquid is sufficient or not by detecting a reflected area of the liquid 10 or a difference of the reflection height sucked into the disposable tip 8 according to increase/decrease of the light amount.

Figure 9:
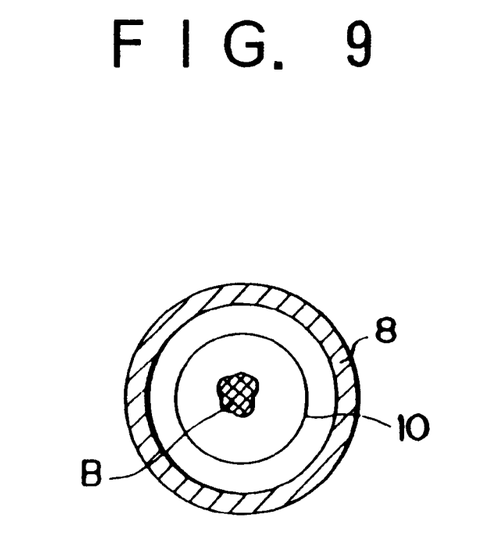
FIG. 9 is an explanatory transverse sectional view showing a state of the surface of a sucked liquid when contamination of a liquid by foreign matters contained therein is detected with the pipetting device according to a ninth embodiment of the present invention.

FIG. 9 shows a ninth embodiment of the present invention, and in this embodiment, in a case where a liquid (blood serum) sucked into a disposable tip 8 is contaminated with foreign matters B such as bubbles or fibrins, a light amount received by the light receiving body 12 varies due to the foreign matters B as compared to that in the normal case, so that successive fluctuations of the light amount due to contamination thereof with the foreign matters B can easily be detected to determine whether or not the liquid is contaminated with the foreign matters B.

Figure 10:
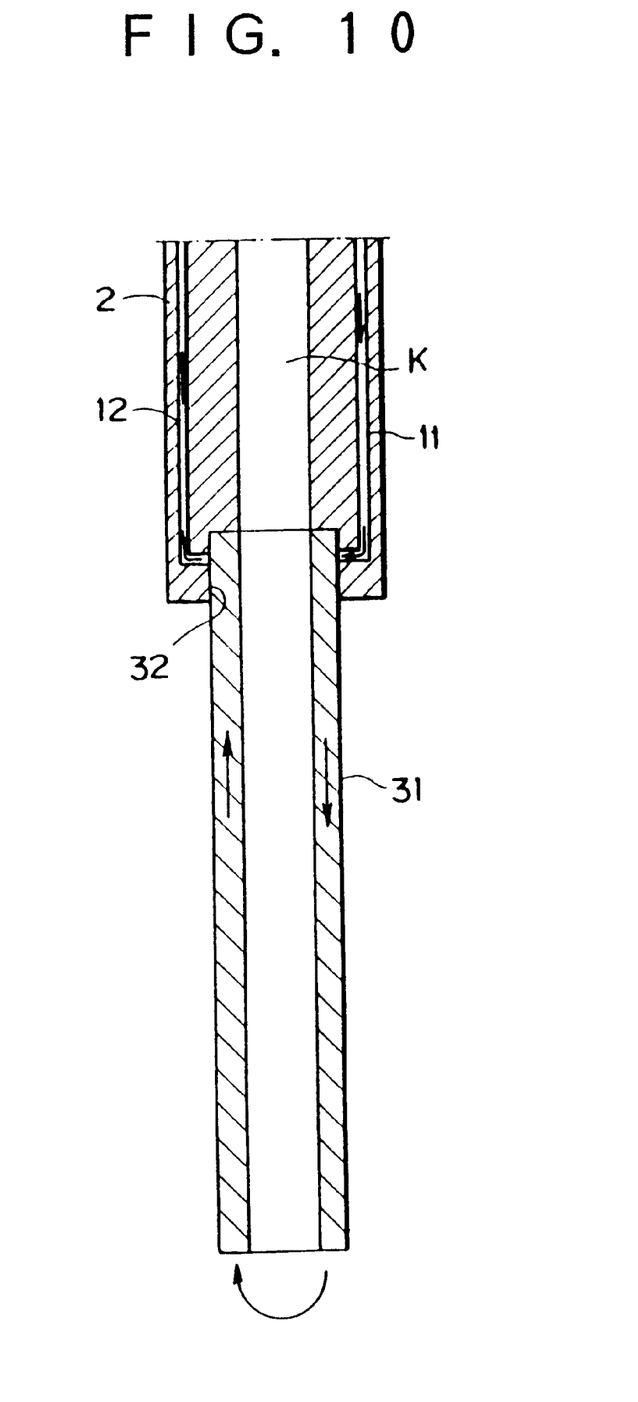
FIG. 10 is an explanatory view showing a transmission path for a light when a cleaning tip of the pipetting device according to a tenth embodiment of the present invention is empty.
Figure 11:
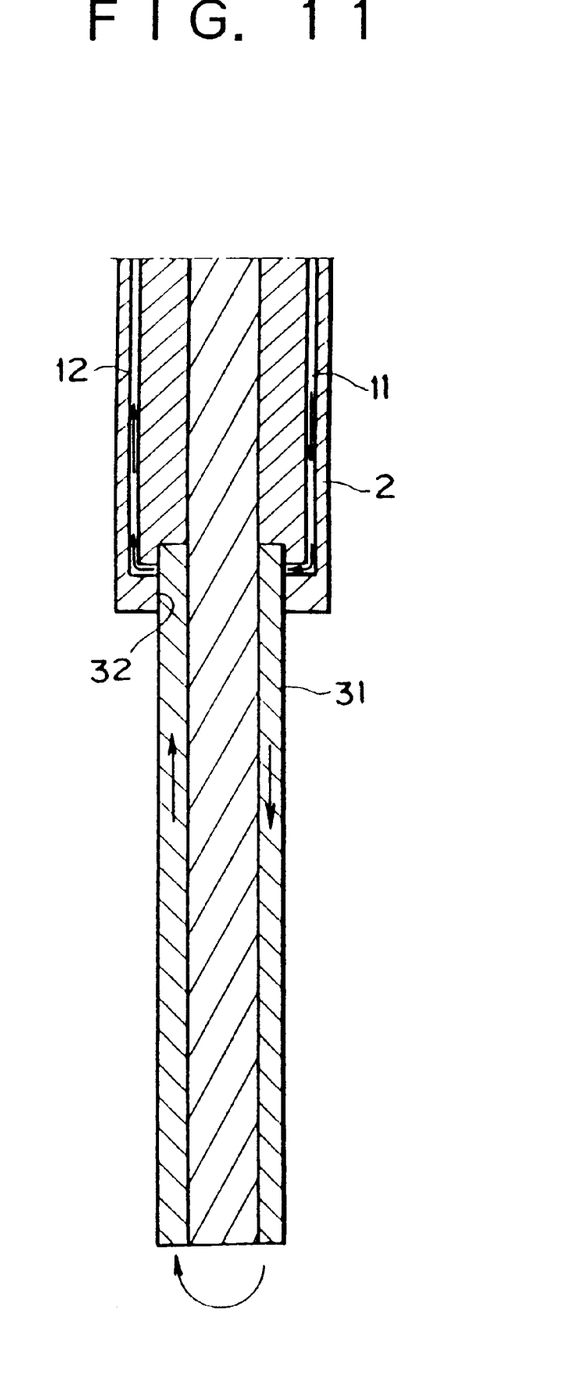
FIG. 11 is an explanatory view showing a transmission path for a light when the inside of the cleaning tip of the pipetting device is filled with a cleaning liquid.

FIG. 10 and FIG. 11 show a tenth embodiment of the present invention, and the embodiment shows a case where an engaging section 32 of the tip 31 of a cleaning system having a reversely convex ring shape is formed at the lower edge section of the nozzle 2, the lower edge sections of the light irradiating body 11 and light receiving body 12 are each exposed to the inside of the engaging section 32, and a light irradiated from the light irradiating body 11 can be engaged in the engaging section 32 of the nozzle 2 and received by the light receiving body 12 through the tip 31 of a cleaning system formed with a transparent material. The other configuration features and effects thereof besides those described above are substantially the same as those in the first embodiment, so that the same reference numerals used in the first embodiment are assigned to the portions corresponding thereto in the figure, and detailed description thereof is omitted herein.

When the tip 31 of a cleaning system is detachably attached to the nozzle 2 as described above, and in a case where the inside of the tip 31 is "empty" as shown in FIG. 10, a light irradiated from the light irradiating body 11 passes through the tip 31 to the opening section of the chip 31 of a cleaning system, again passes through the tip 31 to the light receiving body 12, and is received thereat, so that determination can be made as to whether the tip 31 is "empty (exhausted state) or not by previously measuring an amount of received light in this step.

When the inside of the tip 31 is in a state of being filled with a cleaning liquid as shown in FIG. 11, a light irradiated from the light irradiating body 11 passes through the cleaning liquid from the tip 31, again passes through the tip 31 and is received by the light receiving body 12, so that determination can be made as to whether the tip 31 is filled with a cleaning liquid or not by previously measuring an amount of received light in this step.

However, in the embodiments shown in FIG. 10 and FIG. 11, the outer surface of tip 31 of a cleaning system should preferably be subjected to the same light-proof processing, because thereby the detecting conditions are not affected from outside of the tip 31, so that the detection thereof with higher precision can be executed.

As described above, in the present invention, assuming a case where sucking/determining a liquid level are executed by using a light, a nozzle is used as a light receiving body, which makes it possible to detect the level of the liquid sucked by the nozzle, without being affected by any measuring conditions outside the nozzle tip, and in addition the light receiving body is provided in the nozzle, which makes it possible to prevent without fail generation of cross contamination caused by contacting the light receiving body with a liquid.

In the present invention, not only the liquid level is detected, but also a liquid is filled in a disposable tip or a tip of a cleaning system detachably attached to the nozzle, a light is passed through the liquid in the disposable tip or the tip of a cleaning system, and fluctuation of a light amount of the sucked liquid is detected, so that, for instance, a sucked amount of the liquid, transparency thereof, contamination by bubbles therein, clogging, and a state when water has been exhausted are determined.

Furthermore, in the present invention, fluctuation of a light wave length can be detected and a change of color is checked by the nozzle, whereby a liquid level can also be detected.

In the present invention, a color change can be detected according to the nozzle to detect the color of the colored vessel accommodating a liquid therein through the liquid, or according to the nozzle to detect a color of a rack or a color of a holder in which a transparent vessel accommodating a liquid therein is vertically provided, through the liquid, which makes it possible to detect a liquid level corresponding to a change of color environment outside of the disposable tip.

With the present invention, a color of a blood clot or a blood coagulant can be identified in a process in which the nozzle is moving downward while sucking a blood serum, so that an interface on which layers are separated can easily be detected.

In the present invention, the light is not limited to a case wherein light which is directly received from the disposable tip or from the opening section of the lower end of the tip of a cleaning system attached to the nozzle, and, for instance, a light may be irradiated or received through a transparent disposable tip or a tip of a cleaning system.

In this case, an external surface and/or an internal surface of the disposable tip or the tip of a cleaning system except a portion for transmitting a light is coated with a black film or a mirror film, or the tip is subjected to a light-proof processing such as coloring, whereby fluctuations of the light can be detected with high sensitivity and accuracy.

In the present invention, the nozzle itself is formed with a light transmitting material in a tubular form, and a light irradiating section and a light receiving section are formed in the nozzle formed with the light transparent material, or only the lower edge section thereof is formed with the light transparent material, or optical fibers are provided therein, so that a liquid level can be detected with high-precision without any restriction of liquid sucking operations by the nozzle.

With the present invention, the light receiving edge section of the optical fibers is provided in the bottom surface or the side section of the nozzle, so that reflected light entering into the disposable chip can be captured without fail. It is needless to say that the nozzle is desirably subjected to a light-proof processing.

In the present invention, light supplied from the light irradiating body is not necessarily focused, but depending on conditions such as a form or a length of a chip, a diameter of an opening section, and a light-proof property or the like, a lens body focused at a point where the change of the amount of received light can be checked with high-precision, at the lower end of a disposable tip or a tip of a cleaning system, said point located, for instance, at an internal opening section at the lower end of a disposable tip or at a position slightly lower than a lower edge of the disposable tip, and in this case, a liquid level can be detected with high-precision without any noise therein.

In the present invention, a light is supplied to a liquid contained in a vessel by transmitting it continuously through a nozzle or blinking it in a flashes therethrough or by means of optical filters, or is supplied from the outside of the nozzle.

Data obtained by the method for sucking/determining the level of a liquid having the construction as described above are used as data for controlling a pipetting device in which driving required for pipetting a liquid to cylinders for moving the nozzle upward/downward the nozzle the nozzle as well as for sucking/discharging a liquid is controlled, which makes it possible to realize a high-precision control.

INDUSTRIAL APPLICABILITY

As described above, the method for sucking/determining the level of a liquid according to the present invention and a pipetting device driven and controlled according to the method are applicable for use in procedures such as qualifying, quantifying, separating, and pipetting a specimen or a sample, identifying a liquid level, and checking whether contents of pipetting are satisfied or not in a clinical inspection. In addition, it is applicable to procedures such as qualifying, quantifying, separating, and pipetting a used drug, identifying a liquid level, and checking whether contents of pipetting are satisfied or not in a chemical analysis, for procedures such as qualifying, quantifying, separating, and pipetting a specimen and a sample, identifying a liquid level, and checking whether contents of pipetting are satisfied or not in a DNA analysis, for procedures such as qualifying, quantifying, separating, and pipetting a used drug, identifying a liquid level, and checking whether contents of pipetting are satisfied or not in a system of producing drugs, for procedures such as qualifying, quantifying, separating, and pipetting a specimen and a sample, identifying a liquid level, and checking whether contents of pipetting are satisfied or not in a bacteria and virus inspection, for procedures such as qualifying, quantifying, separating, and pipetting a specimen and a sample, identifying a liquid level, and checking whether contents of pipetting are satisfied or not in a water quality inspection, and furthermore for procedures such as qualifying, quantifying, separating, and pipetting a used drug, identifying a liquid level, and checking whether contents of pipetting are satisfied or not in color synthesis.

I claim:

1. A method for sucking/determining the level of a liquid contained in a vessel by means of a nozzle, comprising the steps of:

receiving a light irradiation proceeding from the liquid near an opening located at a lower end of a disposable tip or a tip of a cleaning system attached to the lower end of said nozzle through a space defined by the said disposable tip or the tip of the cleaning system and entering into the lower end of said nozzle, and detecting fluctuation of said received light irradiation wherein an outer surface of said disposable tip or the tip of said cleaning system is subjected to a light-proof processing.

2. A method according to claim 1, wherein said disposable tip or said tip of a cleaning system is detachably attached to the lower end of said nozzle.

3. A method according to claim 1, wherein said nozzle detects a liquid level in said vessel by detecting when a light reflected from a liquid surface has come into the opening at the lower end of the disposable tip or the tip of the cleaning system.

4. A method according to claim 1, wherein said liquid fills said disposable chip or said tip of a cleaning system attached to said nozzle, and a light is received by said nozzle through said liquid in said disposable tip or said tip of a cleaning system.

5. A method according to claim 4, wherein said nozzle determines a sucking rate of a liquid, its transparency, presence of bubbles therein, and a clogged state or a dry state of the tip by detecting fluctuation of the amount of the received light by the sucked liquid.

6. A method according to claim 4, wherein said nozzle recognizes a change of color by detecting a change of a wave length of the received light.

7. A method according to claim 4, wherein said nozzle detects, through the liquid, the color of a colored vessel containing said liquid therein.

8. A method according to claim 4, wherein said nozzle detects, through the liquid, the color of a rack or a holder, in which a transparent vessel containing the liquid therein is provided in an upright state.

9. A method according to claim 4, wherein said nozzle detects an interface with a solid surface or a liquid surface contacting the bottom surface of the sucked liquid by determining a change in the amount or wave length of the received light when said disposable tip sucks the liquid.

10. A method according to claim 1, wherein said light passes through the disposable tip or the tip of a cleaning system connected to said nozzle.

11. A method according to claim 1, wherein said light-proof processing is a coloring processing.

12. A method according to claim 1, wherein said nozzle is formed in a tubular form with a light transmitting material.

13. A method according to claim 1, wherein at least a lower edge section of said nozzle is formed with a light transmitting material.

14. A method according to claim 1, wherein at least one optical fiber is provided in said nozzle.

15. A method according to claim 14, wherein a light receiving edge section of said at least one optical fiber is provided in a bottom surface or a side portion of said nozzle.

16. A method according to claim 1, wherein said nozzle is subjected to a light-proof processing.

17. A method according to claim 1, wherein a lens is provided in said nozzle, said lens being focused at a position where fluctuations of an amount of the received light around the lower end can be recognized with precision.

18. A method according to claim 13, wherein irradiation of light to said liquid is performed through the nozzle formed with said light transmitting material.

19. A method according to claim 14, wherein irradiation, transmission, and/or reception of light to and from said liquid is performed through an optical fiber for light irradiating and/or an optical fiber for light receiving provided in said nozzle.

20. A method according to claim 1, wherein a source of said light irradiation is located outside of said nozzle.

21. A pipette device, in which the driving force required for pipetting at liquid to cylinders, for moving said nozzle upward/downward, and for sucking/discharging a liquid is controlled, comprising:

a nozzle having an opening section located at a lower end thereof;

a disposable tip or a tip of a cleaning system having a first, upper end attached to the lower end of said nozzle and having a second, lower end adapted to suck liquid thereinto wherein an outer surface of said disposable tip or the tip of said cleaning system is subjected to a light-proof processing;

a light source for irradiating light at said opening section of said nozzle and through an opening at said lower end of said disposable tip or said tip of a cleaning system when bringing said disposable tip or said tip of a cleaning system close to the surface of a liquid contained in a vessel;

a light receiver for receiving light proceeding from the liquid near the opening of said lower end of said disposable tip or said tip of a cleaning system and entering into the opening section of said nozzle; and a light detector for detecting fluctuations of said received light.

22. A method according to claim 1, wherein the light is irradiated when the nozzle is brought close to the surface of the liquid in the container while sucking the liquid.

23. A method according to claim 1, comprising irradiating light through the opening at the lower end of the disposable tip or the tip of the cleaning system attached to the lower end of said nozzle when bringing the disposable tip or the tip of the cleaning system close to the surface of a liquid accommodated in said vessel.

24. A method according to claim 3, wherein light irradiation at the opening located at the lower end of said nozzle is irradiated through the space defined by said disposable tip or the tip of the cleaning system.

* * * * *